United States Patent [19]

Bucalo

[11] 4,206,749
[45] Jun. 10, 1980

[54] CONTROL SYSTEMS AND METHODS UTILIZING MAGNETICALLY RETENTIVE BODIES

[76] Inventor: Louis Bucalo, 155 Roberts St., Holbrook, N.Y. 11741

[21] Appl. No.: 913,329

[22] Filed: Jun. 7, 1978

[51] Int. Cl.² ............................................ A61B 19/00
[52] U.S. Cl. ..................................... 128/1 R; 251/65
[58] Field of Search ............. 128/1 R, 1.3, 1.5, 419 P, 128/419 PG, 419 PT, 2 F, 2 R, 213, 260; 3/1.1, 1.7; 251/65; 335/207, 219, 306

[56] References Cited

U.S. PATENT DOCUMENTS

| | | | |
|---|---|---|---|
| 3,206,160 | 9/1965 | Bennett | 251/65 |
| 3,518,997 | 7/1970 | Sessions | 128/419 PG |
| 3,609,425 | 9/1971 | Sheridan | 251/65 |
| 3,742,933 | 7/1973 | Bucalo | 128/1 R |
| 3,766,928 | 10/1973 | Goldberg et al. | 128/419 P |
| 3,777,737 | 12/1973 | Bucalo | 128/1 R |
| 4,013,063 | 3/1977 | Bucalo | 128/1 R |

*Primary Examiner*—William E. Kamm
*Attorney, Agent, or Firm*—Steinberg & Blake

[57] ABSTRACT

In a control system and method which utilize at least two magnetically retentive bodies, each of which has a given magnetic domain orientation, preferably at least one of these bodies is supported by a supporting structure for movement or balance with respect to the other to assume due to its natural magnetic interaction with the other body a monostable position or force interaction providing between the bodies a first magnetic relationship which achieves a first effect which is monostable under the influence of random disturbances. A structure capable of temporarily creating a polarizing magnetic field of sufficient strength is utilized for changing at least one of the above magnetic domain orientations thereby eliminating the first magnetic relationship. After the polarizing magnetic field has been removed, due to the changed magnetic domain orientation one of the bodies can move with respect to the other, due to natural magnetic interaction therewith, to a second monostable magnetic interrelationship, and this latter second monostable positional or force interrelationship is utilized for achieving a second effect.

32 Claims, 23 Drawing Figures

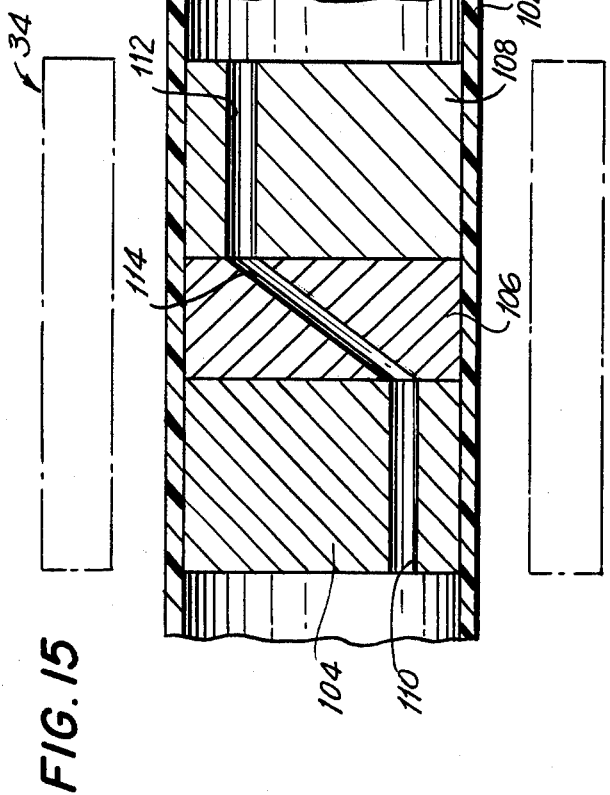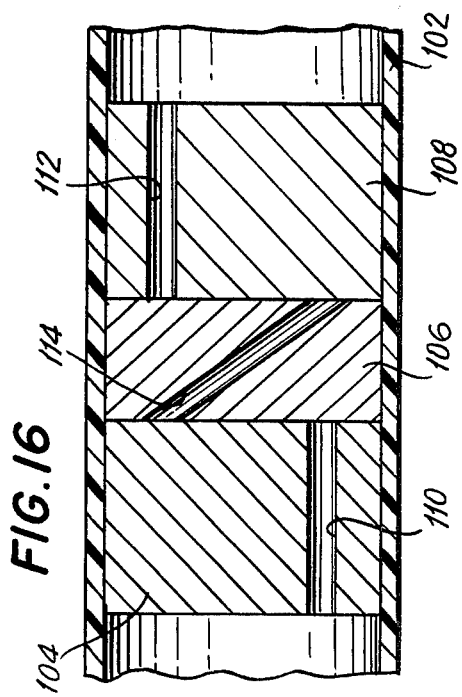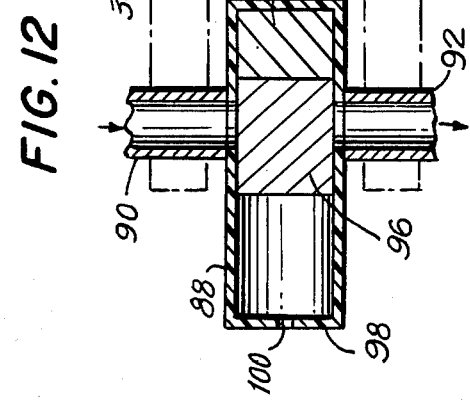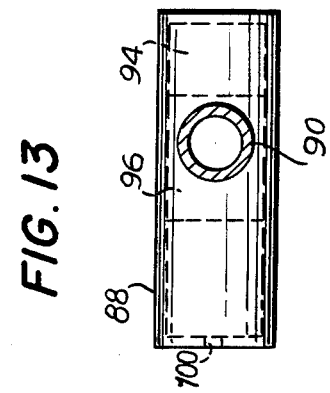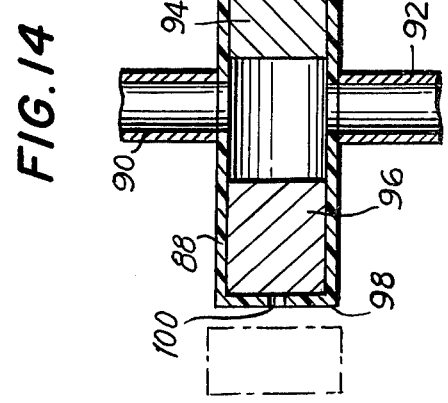

CONTROL SYSTEMS AND METHODS UTILIZING MAGNETICALLY RETENTIVE BODIES

BACKGROUND OF THE INVENTION

The present invention relates to control systems and methods.

In particular, the present invention relates to control systems and methods which utilize magnetically retentive bodies each of which has a given magnetic orientation for reacting magnetically to provide between at least two of these bodies a predetermined positional interrelationship for achieving a predetermined effect.

At the present time there is a requirement in a number of different fields for various types of controls which can only be achieved with conventional methods and structures in a complex, expensive manner. Thus, for example, in order to index a given element to a number of different positions, only relatively complex, expensive systems and methods are available. Also, in connection with controlling the flow of fluids, it is necessary at the present time to utilize relatively complex expensive systems. With respect to fluid flow, control systems and methods are required not only for starting and stopping the flow of a fluid but also for providing different types of flow such as, for example, filtered and unfiltered fluid flow. The presently known methods and systems for achieving such results are easily subject to faulty operation, require a relatively complicated design, and can be changed from one type of operation to another type of operation accidentally.

Although the present invention is applicable to a number of widely differing fields, it is in particular applicable to the reversible prevention of conception by placing in each vas deferens of a male adult a device which can be selectively set either to permit sperm to flow freely so as to enhance the possibility of conception or to prevent sperm from flowing in numbers sufficient to achieve conception. Devices of this type are shown, for example, in U.S. Pat. Nos. 3,991,743 and 4,013,063. The features disclosed in these patents are entirely satisfactory, and the present invention in one of its aspects provides a further development of the features of these patents.

SUMMARY OF THE INVENTION

It is accordingly a primary object of the present invention to provide methods and systems capable of achieving controls in a simple, effective, inexpensive, and fully reliable manner.

It is in particular an object of the present invention to provide monostable methods and systems according to which it becomes possible to provide effective controls under conditions where at least two different effects are required but do not exist as possible conditions simultaneously and therefore cannot be inadvertently created as often happens with bistable systems which do provide for at least two conditions simultaneously. For the purposes of clarity, a bistable system is defined as follows:

A bistable control means is a control means which provides an existing control condition "A" and an existing control condition "B", said bistable control means being capable of randomly being positioned at either control condition "A" or control condition "B" by a random disturbance once said random disturbance is removed.

Reference is made to FIG. 19 in which a control member 152 is positioned at recess A along control surface 151. As a result of a random disturbance of the system of FIG. 19, the control member 152 can be positioned at recess B as shown in phantom lines when the random disturbance is removed.

A monostable control means is a control means which provides a single existing control condition, said monostable control means being self-restoring to said single control condition when a random disturbance is applied and subsequently removed.

A monostable system is shown in FIG. 20. As a result of a random disturbance, the control member 152 can be displaced from position A along surface 153, said control member 152 being self restoring to condition A when the external disturbance is removed.

A similar monostable control system is shown in FIG. 21 to provide a monostable position "B" of control member 152 along control surface 154.

It is an object of the present insertion to provide methods and systems of remotely eliminating the monostable system of FIG. 20 and replace it with the monostable system of 21 for all conditions encountered in service, thereby eliminating the effects of a random disturbance or inadvertent operation of the system.

Thus, it is an object of the present invention to provide methods and systems according to which it becomes possible to effectively achieve controls such as turning a valve on and off according to a predetermined program, mechanically moving a component according to a predetermined program, providing different types of fluid flow such as filtered and unfiltered fluid flow and in particular this latter type of operation in connection with reversible prevention of conception.

According to the method of the invention, at least two magnetically retentive bodies, each of which has a given magnetic domain orientation, provide as a result of the natural magnetic interaction therebetween a first monostable relationship which achieves a first effect. At least one of these magnetic domain orientations is changed by the temporary application of a polarizing magnetic field and then at least one of these bodies is released to move as a result of magnetic interaction with the other body to a position with respect thereto providing a second monostable relationship between the bodies, and this second monostable relationship is utilized for achieving a second effect.

The structure of the invention includes at least two magnetically retentive bodies, each of which has a given magnetic orientation, and a support means which supports at least one of these bodies for movement with respect to the other, as a result of natural magnetic interaction therewith, to a position where these bodies provide a first monostable relationship for achieving a first effect. By way of a magnetic field of sufficient strength to reorient at least one of the magnetic domains to form a new permanent magnet (herein referred to as a polarizing magnetic field), a polarizing magnetic field is directed through the bodies for changing at least one of the magentic domain orientations, and upon termination of the polarizing magnetic field, one of the bodies moves with respect to the other to provide therebetween a second monostable relationship capable of achieving a second effect. It is noted that a polarizing magnetic field is generally of the order of 15,000 oersteds applied for a few milliseconds and such a polarizing magnetic field cannot practically be provided by a permanent magnet or for a longer period of time without incurring extremely high forces and energy levels.

Whereas the system is most advantageous to providing a positional relationship between components of a given assembly, it is applicable to force balance mechanisms wherein none of the components are permitted to move, but interactive forces produced between the members provides useful force or torque relationships.

BRIEF DESCRIPTION OF DRAWINGS

The invention is illustrated by way of example in the accompanying drawings which form part of this application and in which;

FIG. 12 schematically illustrates in a sectional elevation a further embodiment of a structure utilizing the method and system of the invention with a polarizing magnetic field creating means being indicated in phantom lines in FIG. 12;

FIG. 13 is a schematic top plan view of the structure of FIG. 12;

FIG. 14 is a schematic sectional elevation showing the position assumed by components of FIG. 12 after application and removal of a polarizing magnetic field in accordance with the invention, with FIG. 14 also showing the polarizing magnetic field creating means in phantom lines;

FIGS. 15 and 16 are schematic longitudinal sectional elevations of a method and system of the invention utilized for achieving non-filtered and filtered fluid flow;

DESCRIPTION OF PREFERRED EMBODIMENT

Figure 1:
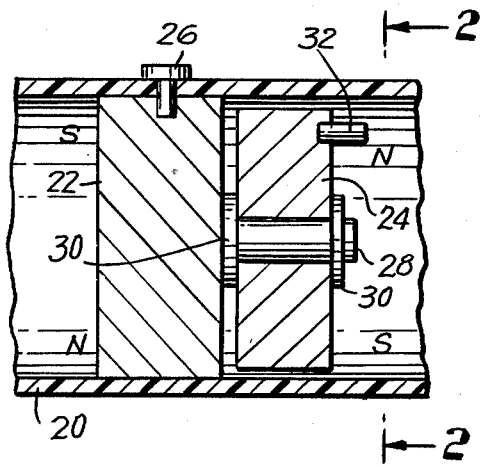
FIG. 1 is a fragmentary longitudinal sectional elevation schematically illustrating the principle of operation of the method and system of the present invention.
Figure 2:
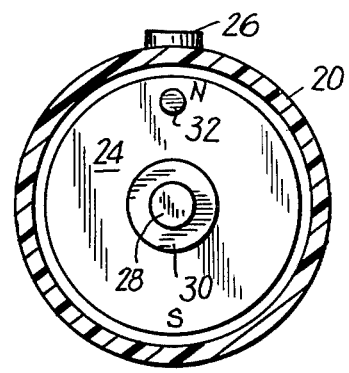
FIG. 2 is a transverse section of the structure of FIG. 1 taken along line 2—2 of FIG. 1 in the direction of the arrows.

Referring to FIG. 1, there is schematically illustrated therein a support means which includes, as a part thereof, a non-magnetic tubular housing 20. Within this housing 20 are situated a pair of magnetically retentive bodies 22 and 24. Magnetically retentive bodies are bodies which will retain a given magnetic domain although this domain can be changed by situating the body in a polarizing field of sufficient strength. However, once the magnetic retentive body has a given magnetic domain it will retain this domain until the latter is changed as by way of a sufficient strength polarizing field. In the illustrated example these bodies are in the form of solid cylinders. The magnetically retentive material of the bodies 22 and 24 may be materials such as alloys of platinum-cobalt or iron-cobalt-vanadium. As is well known, such magnetically retentive bodies are capable of being magnetically oriented in a predetermined manner while at the same time the magnetic domain orientation can be changed for isotropic materials and is difficult to change for anisotropic materials. In the particular example shown in FIG. 1 the magnetically retentive body 22 has a magnetic orientation according to which the south pole of the body 22 is situated at the upper part thereof, as viewed in FIG. 1, and the north pole is situated at the lower part thereof. On the other hand, the body 24 has a magnetic orientation according to which the north pole is situated at the upper part thereof and the south pole is situated at the lower part thereof, as is apparent from FIGS. 1 and 2.

In the particular example illustrated in FIG. 1, the support means which includes the tubular housing 20 maintains the body 22 stationary, as by way of a schematically illustrated set screw 26. On the other hand, the support means includes a shaft 28 fixed coaxially to the body 22 and projecting therefrom through an axial bore passing through the body 24 so that the latter is supported for free rotation, being maintained on the shaft 28 against axial movement with respect thereto by way of suitable collars 30. This body 24 is freely turnable within the tubular housing 20 so that it naturally assumes by magnetic interaction with the fixed body 22 the angular position illustrated where the north pole of body 24 is aligned with the south pole of the body 22 while the south pole of the body 24 is aligned with the north pole of the body 22. Simply in order to indicate the angular position of body 24 with respect to body 22, body 24 has a projection 32 which it will be noted is situated at the upper part of the body 24 when the latter provides with the body 22 the positional relationship between these bodies 22 and 24 illustrated in FIG. 1. This positional relationship between the bodies 22 and 24 may be utilized to achieve any one of a number of different effects, as will be apparent from the description which follows.

In order to change the particular positional relationship of the bodies 22 and 24 shown in FIG. 1, at least one of the magnetic orientations is changed. For this purpose, as shown schematically in FIG. 3, a polarizing magnetic field creating means 34 is positioned close enough to the schematically illustrated bodies 22 and 24 for directing therethrough, in a direction normal to the common axis thereof, a polarizing magnetic field 36 which is schematically illustrated in dotted lines and which creates an upper north pole and a lower south pole so that in the illustrated example the magnetic orientation of body 22 remains unchanged while the magnetic orientation of body 24 is changed to be the same as that of the body 22. As is shown in FIG. 4, the polarizing magnetic field creating means 34 includes any suitable support structure 37, shown in phantom lines, carrying a pair of coils 38 which by way of the support structure 37 can be situated with respect to the bodies 22 and 24 in the position indicated in FIGS. 3 and 4. The positions indicated by FIG. 3 exist only during the pulsation of the polarizing magnetic field. The coils 38 are connected in series to a source of current 40, and the illustrated circuit be opened and closed by way of a switch 42. It will be understood that the source of power 40 and the switch 42 can be situated at a location remote from the bodies 22 and 24 while through flexible conductors the support structure 37 can be connected to the source of power and the switch while carrying the coils 38 at locations spaced from each other in the manner shown in FIGS. 3 and 4 to enable these coils to be positioned with respect to the bodies 22 and 24 in the manner illustrated. Thus, upon closing of the switch 42 the magnetic field 36 will be created for changing the magnetic orientation of the body 24 in the illustrated example. The switch 42 is only schematically illustrated. The switch 42 is closed only momentarily for a relatively short interval which will provide the field 36 in the form of a pulsation which will substantially instantaneously change the magnetic orientation of the magnetically retentive body 24.

Figure 5:
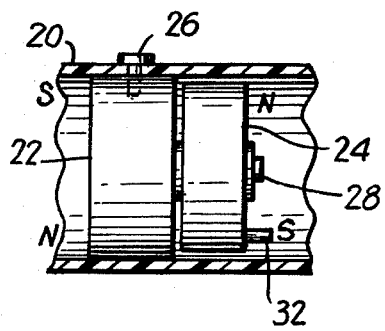
FIG. 5 schematically illustrates the result of the change of the magnetic domain caused by the polarizing magnetic field as illustrated in FIGS. 3 and 4 after the polarizing magnetic field is removed.

As soon as the polarizing magnetic field 36 terminates, the body 24 is released from the influence of the magnetic field while still retaining its changed magnetic orientation, so that upon termination of the magnetic field 36 the body 24 immediately turns through 180° around the shaft 28, assuming now the position schematically indicated in FIG. 5 where the body 24 has been displaced angularly through 180° with respect to the body 22, as compared with the positional relationship between these bodies shown in FIG. 1. The termination of the magnetic field 36 releases the body 24 so that as a result of natural magnetic interaction with the fixed body 22 it is possible for the body 24 to assume automatically the angular position shown in FIG. 5 where a second positional relationship is provided between the bodies 22 and 24, and it will be seen that the projection 32 is now situated at the lower part of the body 24. This second positional relationship shown in FIG. 5 is utilized in any one of a number of different ways to achieve a second effect, as will be apparent from the description which follows.

Figure 3:
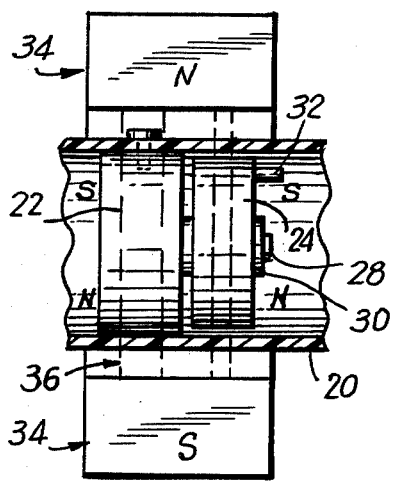
FIG. 3 is a schematic illustration of application of a magnetic field to the structure of FIG. 1.
Figure 4:
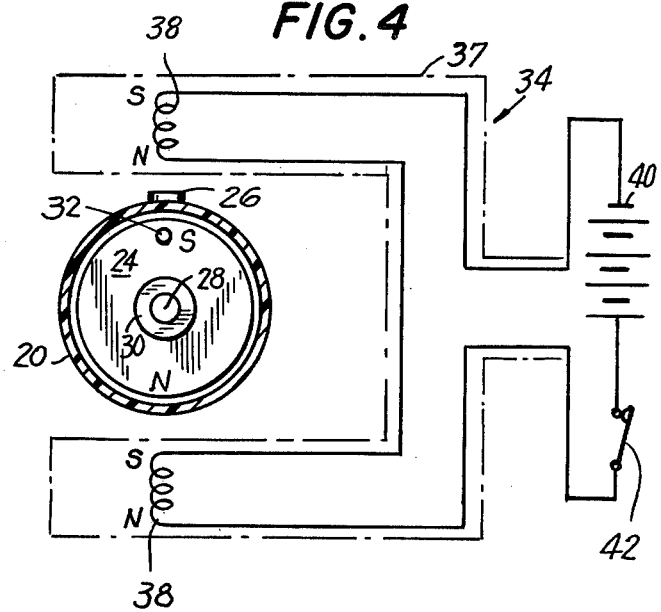
FIG. 4 is a side elevation schematically illustrating further details of the application of one type of polarizing magnetic field in the arrangement shown in FIG. 3.

It will be noted that with the above method and system of the invention, the changed magnetic orientation of body 24 provided by way of the polarizing magnetic field 36, as shown in FIG. 3, rotates body 24 to the initial relative orientation with body 22 as indicated in FIG. 1. Thus, upon termination of the polarizing magnetic field 36, the body 24 immediately turns through 180° to restore the body 24 to its initial magnetic relationship with body 22, even though the body 24 now has with respect to the body 22 a positional relationship different from that shown in FIG. 1. Thus, the method and systems of the invention as shown in FIGS. 1–5 and described above is a monostable control method and system in the sense that predetermined relative positions are always provided unless an external force such as a torque is applied, and upon elimination of this external torque, the system is self-restoring to the initial control condition according to which the same physical orientations are restored after the torque has been eliminated.

It is noted that if both 22 and 24 are made of isotropic materials the plane of the polarizing magnetic field could be at an angle with respect to the plane of FIG. 3 and body 24 would still rotate 180° with respect to body 22 if both bodies are subject to the polarizing magnetic field. This fact is very important for practical systems which exist at an unknown angular orientation within a sealed housing.

It is possible under certain special conditions to utilize the method and system of the invention with one anisotropic body in which the magnetic poles can only extend in a certain direction and therefore the plane of magnetization cannot be changed. Thus by utilizing one anisotropic material for body 22 and one isotropic material for body 24 is is not essential to provide an arrangement as shown in FIG. 3 where the polarizing field is in the plane of the drawing. If, for example, the magnetic field creating means 34 is oriented in the position displaced by 90° from the position thereof shown in FIG. 4, then the magnetic field 36 would provide north and south poles which are in a horizontal plane on body 24, rather than a vertical plane as illustrated, and under these conditions when the magnetic field 36 terminates the body 24 would turn only through 90°.

Furthermore, it is not essential to change the magnetic orientation of the movable body. Thus the magnetic field creating means 34 could be reversed so that it would provide an upper south pole and a lower north pole, thus maintaining the magnetic orientation of the movable body 24 unchanged while reversing the polarity of the stationary body, and under these conditions also when the magnetic field terminates the movable body 24 would turn through 180°.

Many variations are possible by using two isotropic materials, or one isotropic material and one anisotropic materials, and by varying the coverage of the field of the polarizing magnetic field.

One of the advantages achieved with the method and system of the invention results from the fact that the method and system of the invention are predictable. As a result of this characteristic, it is possible to maintain the polarizing magnetic field creating means 34 at a position such as that shown in FIG. 4, and the switch 42 can be opened and closed at regular predetermined intervals, with the result being that the body 24 will turn at given intervals through 180° without requiring any change in the position of the magnetic field creating means 34. Thus, because of this monostable feature of the invention it is possible to provide an exceedingly simple structure of achieving a series of movements of a member such as the member 24. The timing of these movements of course can easily be controlled by proper timing of the closing and opening of the switch 42. Of course, the polarizing magnetic field can be created by a capacitor discharge energy supply to supply a pulse of polarizing magnetic field.

Figure 7:
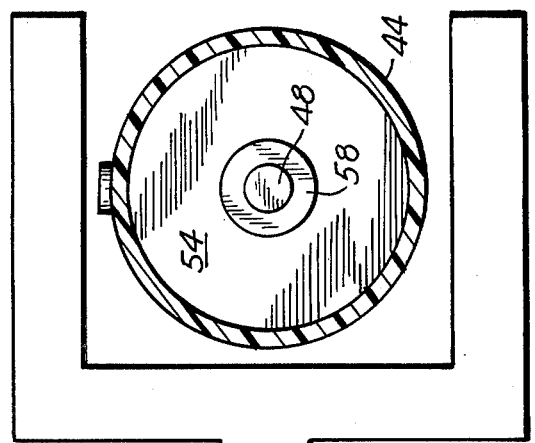
FIG. 7 schematically illustrates how a polarizing magnetic field is applied to the arrangement shown in FIG. 6.
Figure 6:
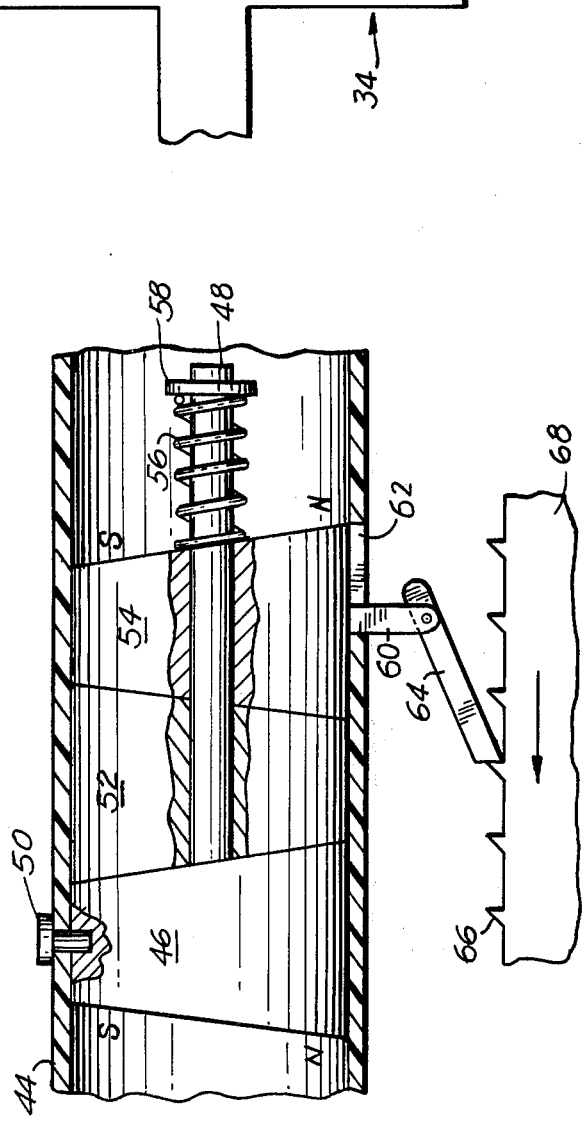
FIG. 6 is a fragmentary schematic partly sectional elevation showing one type of application of the method and system of FIGS. 1–5.
Figure 8:
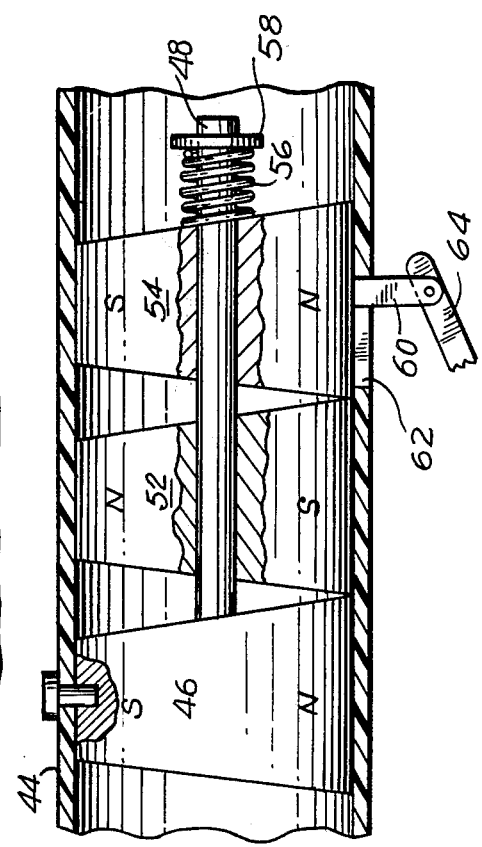
FIG. 8 illustrates a position occupied by the components of FIG. 6 after application and removal of the magnetic field.

FIGS. 6–8 schematically illustrate one possible application of the method and system of the invention. Thus, as is schematically illustrated in FIG. 6, a non-magnetic tubular housing 44 fixedly carries in its interior a magnetically retentive body 46 which is cylindrical but has oppositely inclined end faces, although if desired only the right end face of the body 46 need be inclined as illustrated. The support means of this embodiment includes in addition to the housing 44 an elongated shaft 48 fixed to and projecting axially from the body 46 which is fixed to the housing 44 as by a set screw 50. The shaft 48 extends through coaxial bores of a pair of magnetically retentive bodies 52 and 54 which may be identical with the body 46 except for the bores passing through the bodies 52 and 54. A spring 56 is coiled around the shaft 48 and urges the bodies 52 and 54 toward the body 46, a suitable nut 58 being threaded onto the shaft 44 for adjusting the compression of the spring 56. The body 54 fixedly carries a downwardly extending lug 60 which passes freely through an axially extending slot 62 formed in the housing 44, and this lug 60 is pivotally connected with an elongated pusher bar 64 capable of cooperating with the teeth 66 of a member 68 which is to be indexed.

The bodies 46 and 54 have identical magnetic orientations according to which, for example, they have as viewed in FIG. 6 upper south poles and lower north poles. Of course the intermediate body 52 will have an upper north pole and lower south pole as a result of its magnetic interaction with the bodies 46 and 54 both of which cannot rotate.

Assuming that the polarizing magnetic field creating means 34, which may be the same as that of FIG. 4, is applied to the system of FIG. 6 in the manner indicated in FIG. 7, then the switch 42 of the magnetic field creating means can be closed to change the magnetic orientation of the intermediate body 52, (or of all three bodies 46, 52, 54) and upon termination of the polarizing magnetic field this body 52 will immediately turn 180° to provide the positions of the components as illustrated in FIG. 8. Thus, the bodies 52 and 54 because of their oppositely inclined end faces move apart from each other and to the right from the body 46, causing the lug 60 to be displaced toward the right, and thus pulling the pusher bar 64 to the right so that its free end moves beyond the next tooth of the member 68. Thus, the magnetic field creating means 34 remains in the position shown in FIG. 7 and at the next pulse the body 52 will return to the position thereof shown in FIG. 6, with the spring 56 expanding so that the pusher bar 64 will now advance the member 68 through a given increment.

In this way, a method and system as shown in FIGS. 6–8 can be used for indexing the member 68 according to a predetermined program. This member 68 may be a turntable which turns sequentially to different operating stations, or it may be an endless chain which is moved by given increments to achieve predetermined controls. If desired the lug 60 can be used simply for opening and closing certain switches or for operating certain valves as this member 60 moves with the body 54. Thus a wide variety of controls can be achieved with a method and system of the invention as shown in FIGS. 6–8 and these controls can be actuated through a sealed barrier or vacuum.

Figure 9:
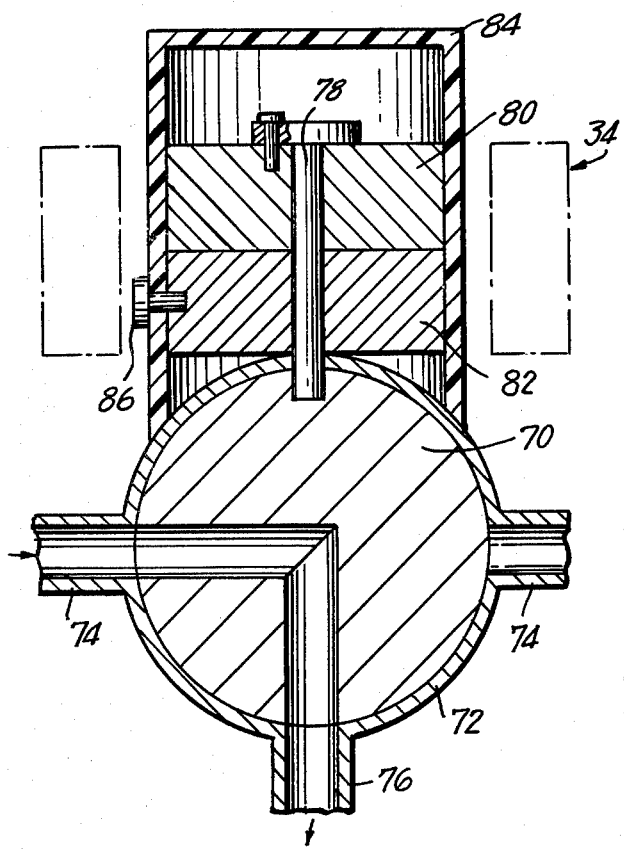
FIG. 9 is a schematic sectional elevation illustrating how the principles of the invention can be applied to a valve.
Figure 11:
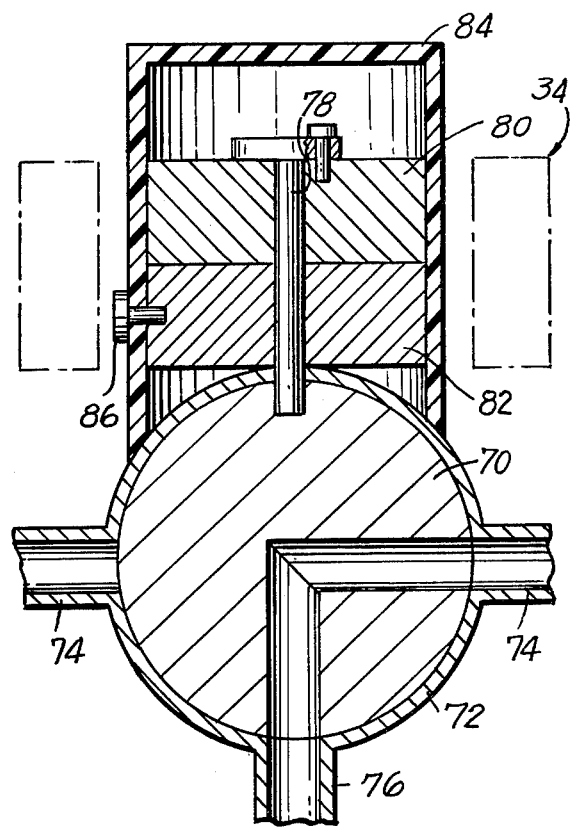
FIG. 11 while also showing the polarizing magnetic field creating means in phantom lines illustrates schematically the position which the valve of FIG. 9 assumes after application and removal of a polarizing magnetic field.
Figure 10:
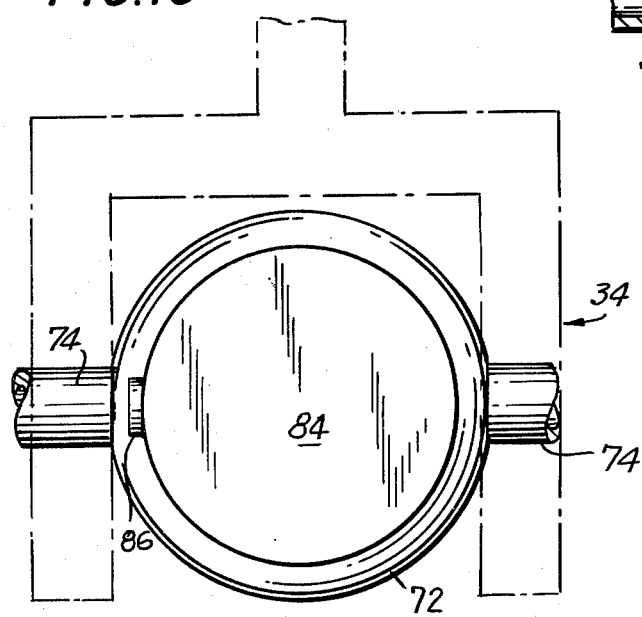
FIG. 10 schematically illustrates how a polarizing magnetic field is applied for changing the magnetic domain of at least one component of the valve of FIG. 9, with FIG. 9 showing in phantom lines how the magnetic field creating means of FIG. 10 is positioned with respect to the structure of FIG. 9.

FIGS. 9–11 illustrate how the method and system of the invention may be utilized for rotating another component. Thus, FIG. 9 shows a rotary ball valve member 70 situated in a spherical housing 72 which communicates with a supply pipe 74 and a discharge pipe 76. The valve is shown in FIG. 9 in its left position where the passage in the valve member 70 provides communication between the pipes 74 and 76. The valve member 70 is fixed to a valve stem 78 which in turn is fixed to a rotary magnetically retentive cylindrical body 80 corresponding to the body 24 of FIG. 1. This body 80 is situated over a similar fixed body 82 which corresponds to the stationary body 22 of FIG. 1, these bodies 80 and 82 being situated within a housing 84 which of course is non-magnetic in the same way as the valve housing 72. The body 82 is fixed to the housing 84 as by a set screw 86. A polarizing magnetic field creating means 34 cooperates with this structure of FIGS. 9–11 in the manner shown in phantom lines. Thus, when the switch 42 of the means 34 is closed the magnetic field referred to above will be provided, and upon termination of this polarizing magnetic field, when the switch 42 opens, the body 80 will turn 180° so as to displace the valve member 70 from the position of FIG. 9 to that of FIG. 11, and now the valve is directed to the right. Upon the next closing and opening of the switch 42 the valve 70 will of course be returned to the left position thereof shown in FIG. 9. Thus it is easily possible with the method and system of the invention to control fluid flow in the manner shown in FIGS. 9–11.

FIGS. 12–14 show a non-magnetic housing 88 which is of a rectangular configuration and which has its interior communicating with a pair of pipes 90 and 92 through which a fluid is adapted to flow. For example the pipe 90 is a supply pipe for supplying a liquid to the pipe 92 which is a discharge pipe. The housing 88 has in its interior a pair of magnetically retentive bodies 94 and 96 which may be identical and which are of a rectangular configuration, the body 94 being fixed while the body 96 is free to slide to the left and right as viewed in FIGS. 12–14.

If it is assumed that the bodies 94 and 96 have magnetic orientations according to which unlike poles are situated at the adjoining surfaces of the bodies 94 and 96, then of course these bodies attract each other, so that the body 96 by attraction to the body 94 remains in the position shown in FIGS. 12–13 where the pipes 90 and 92 do not communicate with each other.

As shown in phantom lines in FIG. 12, a magnetic field creating means 34a, which may be the same as the magnetic field creating means 34 except perhaps it has a different size, can be situated in the position indicated in FIG. 12, and when the switch of the magnetic field creating means is closed to create the magnetic field, this field will pass vertically through the bodies 94 and 96, as viewed in FIG. 12, to provide them with like poles at their adjoining surfaces. When this magnetic field is terminated, the bodies 94 and 96 will thus repel each other, so that now they will assume the position indicated in FIG. 14, and thus the valve is opened and the pipes 90 and 92 communicate with each other.

It will be seen that this system differs from those described above in that the magnetic relationship of the bodies 94 and 96 is changed to maintain the repulsion between the bodies 94 and 96 which maintains them in the position shown in FIG. 14.

Now when it is desired to return the parts to the position of FIG. 12, a magnetic field creating means 34b must be arranged as shown in phantom lines in FIG. 14, to provide a horizontal magnetic field, a viewed in FIG. 14, thus creating at the end faces of the bodies 94 and 96 which are directed toward each other and which are nearest to each other unlike poles, so that when this magnetic field is terminated the body 96 will be attracted back to the body 94, thus returning the parts to the position shown in FIG. 12.

It is possible with an arrangement as shown in FIGS. 12-14 to maintain one magnetic field creating means 34a in the position shown in FIG. 12 and the other magnetic field creating means 34b in the position shown in FIG. 14, and then the magnetic fields can be applied and terminated in a given sequence so as to cause repeated cyclical movement of the body 96 with respect to the body 94 in the manner described above, but it is apparent that this system is not as advantageous as a switch system using a single source of polarizing magnetic field.

FIGS. 15 and 16 illustrate how the method and system of the invention may be utilized to achieve on-off fluid flow. Thus, FIGS. 15 and 16 show a non-magnetic tubular housing 102 which may be similar to the tubular housing 44 of FIG. 6. In this housing 102 are situated three magnetically retentive bodies 104, 106, and 108, which are respectively similar to the bodies 46, 52 and 54 except that the bodies of FIGS. 15 and 16 are not of the wedge-shaped configuration of the bodies of FIGS. 6 and 8. Thus the bodies 104, 106, and 108 have flat end faces which are normal to the common axis of these bodies. The bodies 104 and 108 are fixed in the housing 102 while the body 106 is turnable therein about the common axis of the bodies, this common axis coinciding with the axis of the tubular housing 102. Moreover, the bodies 104, 106 and 108 are solid bodies which are impermeable to fluid flow.

The bodies 104 and 108 are formed with bores 110 and 112, respectively, passing therethrough in a direction parallel to the common axis of these bodies while being spaced from this common axis and being out of alignment with each other as illustrated. On the other hand, the body 106 is formed with a bore 114 passing diagonally therethrough.

In the position of the parts shown in FIG. 15, the bore 114 provides communication between the bores 110 and 112 so that fluid flow is provided, assuming that a fluid of any type flows thorugh the tubular housing 102. These bodies 104, 106 and 108 may be considered as having the same magnetic orientations as the bodies 46, 52 and 54 of FIG. 6.

When it is desired to stop the fluid flow, a polarizing magnetic field creating means 34 is applied in the same way as described above in connection with FIGS. 6-8, and when the polarizing magnetic field is terminated the body 106 will of course turn through 180° to assume the position shown in FIG. 16. Thus in the position shown in FIG. 16, the bore 114 no longer provides a communication between the bores 110 and 112, and thus fluid flow from one to the other of the bores 110 and 112 is prevented. Of course at the next application and termination of the polarizing magnetic field it is possible to return the body 106 to the position shown in FIG. 15, so that with the arrangement of FIGS. 15 and 16 it is easily possible to change from flow to no flow.

Figure 17:
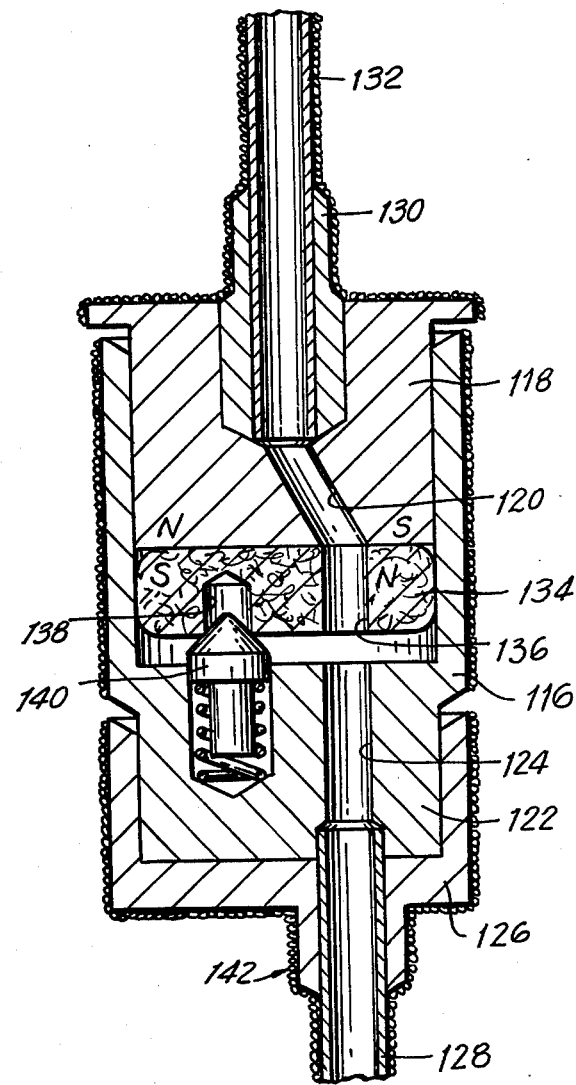
FIG. 17 is a sectional elevation of a device to be situated in a vas deferens for reversible prevention of conception while utilizing the method and system of the invention.

A particular application of the monostable method and system of FIGS. 15 and 16 is illustrated in FIG. 17. Thus, FIG. 17 shows a non-magnetic housing 116 which has at its upper end region as viewed in FIG. 17 a tubular portion fixedly receiving a magnetically retentive body 118, this body 118 being formed with a passage 120 extending therethrough as illustrated. This passage 120 is inclined away from the common axis of the housing 116 and the body 118 so as to terminate at the bottom end of the body 118, as viewed in FIG. 17, at a location spaced from the common axis of the housing 116 and body 118. The housing 116 has spaced from the body 118 a relatively thick end wall 122 which is formed with a passage 124 which is aligned with the inner end of the passage 120 as illustrated. At the outer lower end region of the housing 116, as viewed in FIG. 17, this passage 124 is inclined so as to be situated at the axis of the housing 116. This end wall 122 fixedly and fluid-tightly carries a cap 126 which is formed with an axial bore which receives in its interior in a fluid-tight fixed manner an end region of an elongated tube 128 which is adapted to be placed in a portion of a vas deferens.

In a similar manner the outer portion of the bore 120 of the magnetically retentive body 118 extends along the axis of the body 118 and fluid-tightly carries a tubular member 130 which is non-magnetic and which is fixed fluid-tightly at its interior to an outer end surface region of an elongated tube 132 which is adapted also to be situated in the interior of another portion of the vas deferens.

In the space between the end wall 122 and the magnetically retentive body 118, the housing 116 accommodates a filter body 134 which is also magnetically retentive. The filter body 134 is in a known way provided with a porosity which is sufficiently fine so that while the fluid in which sperm are suspended can pass through the filter body 134, sperm will be retained thereby. The filter body 134 is in the form of a circular disc which can freely turn about the common axis of the body 134 and the housing 116. This filter body 134 is formed with a bore 136 passing therethrough at the same distance from the common axis of the bodies 118 and 134 and housing 116 as the inner lower end of the passage 120, as viewed in FIG. 17. Thus in the position of the parts shown in FIG. 17, the passage 120 communicates with the passage 136 which in turn is coaxially aligned with the bore 124, so that is is possible for sperm suspended in the vas fluid to travel freely through the device shown in FIG. 17 when the components thereof have the position shown in FIG. 17.

The rotary filter body 134 is formed with a detent recess 138 receiving a low force spring detent 140 carried by the end wall 122 of the housing 116. While the spring detent cannot overcome the natural alignment of the monostable system, it has been found advantageous to minimize cumulative errors which can result from multiple sequential reversals as well as provide a detectable position signal as discussed below. This detent recess 138 is diametrically opposed to the bore 136 and situated at the same distance from the axis of the body 134 as the bore 136. Thus the spring detent 140 cooperates with the recess 138 to provide a precise determination of the position of the body 134. The magnetic orientations of the magnetically retentive bodies 118 and 134 may be as illustrated in FIG. 17. Also it is only the bodies 118 and 134 which need be made of a magnet material, the remaining structure of FIG. 17 being non-magnetic. The exterior surfaces of the structure shown in FIG. 17, including the housing 116, the tubular components 132, and the components 130 and 126 may be provided with a tissue ingrowth means 142, in the form of fine gold wire wrapped around and situated against the structure as illustrated, so that tissue in the body will grow into the interstices between the wire portions which form the ingrowth means 142 in order to provide a secure mounting of the device of FIG. 17 in the body. It may be assumed that the sperm-carrying vas fluid flows upwardly as viewed in FIG. 17 from the tube 128 through the bore 124 and the bore 136 of filter body 134 into the bore 120 and then along the tubular member 132.

Assuming that it is desired to place the structure of FIG. 17 in a conception-preventing position, then it is only necessary to apply a polarizing magnetic field through the bodies 118 and 134 in the manner described above in connection with FIG. 1, so that upon termination of this magnetic field body 134 will turn through 180° from the position shown in FIG. 17, and of course the spring detent 140 will now enter into a portion of the bore 136 in order to more precisely align the member 134. In this latter position of course the vas fluid must travel through the filter body 134 which has a porosity fine enough to retain sperm in numbers sufficient to prevent conception.

When it is desired to resume a condition where conception is desired rather than prevented, it is only necessary to apply again a polarizing magnetic field in the form of a pulse which will cause the body 134 to return to the position shown in FIG. 17.

This arrangement of FIG. 17 is of a particular advantage in connection with reversible prevention of conception since an individual provided with devices as shown in FIG. 17 need only visit a physician who can by manipulation tactically situate the device of FIG. 17 between the coils of a unit such as the polarizing magnetic field creating means 34, without requiring any cutting or other surgical procedure for this purpose. Then the magnetic field creating means is operated to create the polarizing magnetic field which will change the position of the body 134, so that in this simple way it is possible to change in the physician's office in a minimum of time and with a maximum of convenience between a condition preventing conception and a condition permitting conception.

Figure 18:
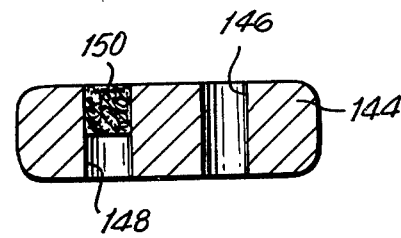
FIG. 18 shows another embodiment of a movable magnetically retentive body which may be utilized in the structure of FIG. 17.
Figure 19:
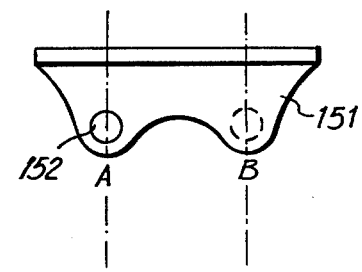
FIGS. 19–21 illustrate bistable and monostable systems.
Figure 20:
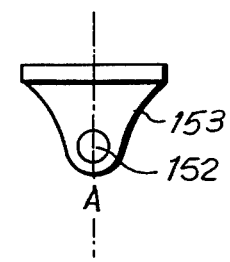
Figure 21:
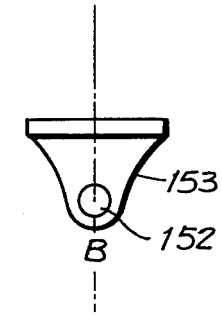

FIG. 18 shows a variation of the body 134 of FIG. 17. Thus in FIG. 18 there is shown a magnetically retentive body 144 of the same size and shape as the body 134, this body 144 having a bore 146 which is identical with the bore 136. However, instead of a detent recess 138, the body 144 has a second bore 148 passing therethrough, and in this second bore there is tightly situated a filter plug 150 which has the same capability as the filter body 134 to permit flow of vas fluid therethrough while preventing travel of sperm therethrough in numbers sufficient for conception.

Thus, if the body 134 is replaced by the fluid impermeable body 144, then when the magnetic orientations position passage 146 in line with passage 120 there will be no obstruction to sperm flow and the spring-pressed detent will enter bore 148. On the other hand, when the magnetic forces situate the filter 150 in the path of flow, so that the fluid in which the sperm are suspended can flow through the filter while the sperm are prevented from flowing with this fluid in numbers sufficient for conception then detent 140 will enter bore 146.

Of course, a construction as shown in FIG. 18 may be utilized to replace the body 106 of FIGS. 15 and 16. Also, the use of a spring detent, although shown only in FIG. 17, a generally applicable to minimize a cumulative angular error caused by repetitive cycling and may be used with any of the above embodiments where a body is to be more precisely positioned repetitively. In effect, the magnetic forces create 99% of the alignment and the detent the remaining 1% of the alignment.

Of course it is to be understood that the construction shown in FIGS. 17 and 18 is illustrated at an enlarged scale inasmuch as the actual device which is implanted in the vas is exceedingly small with the bodies 134 and 144 having the construction of relatively small wafers.

It is thus apparent that by way of the simple, inexpensive methods and systems of the invention it is possible to achieve a wide variety of monostable controls in a reliable, convenient manner.

Figure 22A:
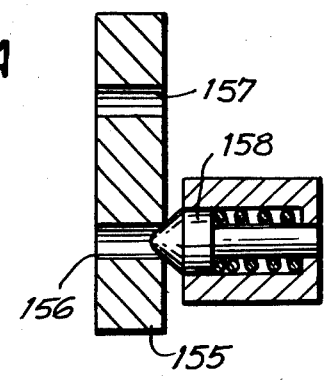
FIG. 22 illustrates remotely detectable detent positions.
Figure 22B:
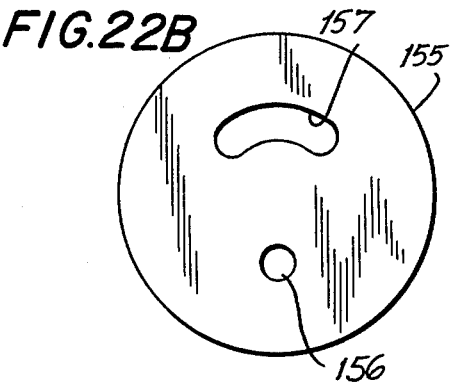

The arrangement of FIG. 22 illustrates a variation of the detent mechanism which is useful for remotely verifying the position of the moveable member 155 in a sealed system years after it has been magnetized to its monostable state at which time verification of the monostable state could be made in the event that medical records are unavailable. Application of a random disturbance, such as a cyclical vibration will automatically vibrate the detent pin 158 in the monostable detent hole. If this monostable position represents detent hole 156, the resultant vibration will be characterized by the small clearances provided between hole 156 and detent 158. If this monostable position represents detent oval hole 157, the resultant vibration will be characteristic of the large clearances provided and the different vibration characteristics can be detected.

What is claimed is:

1. In a control method, the steps of providing between at least two suitably supported magnetically retentive bodies, each of which has a given magnetic domain orientation, a first precise stable relationship resulting from natural magnetic interaction of said bodies which relationship is stable under the influence of random disturbances, while achieving a first effect from said first stable relationship, then changing the magnetic domains of at least one of said magnetic orientations by a sufficient force which is greater than that of random disturbances, permitting at least one of said two bodies to move, due to natural magnetic interaction of said bodies resulting from the changed magnetic domain orientation, to a relationship with respect to the other of said bodies which provides between said bodies a second precise stable relationship, while achieving a second effect from said second stable relationship.

2. In a method as recited in claim 1 wherein said relationships are positional relationships and including the step of directing temporarily through at least one of said bodies a polarizing magnetic field strong enough to change at least said one magnetic domain orientation thereby eliminating the first stable positional relationship, and terminating said magnetic field for permitting said one body to move with respect to said other body to provide said second precise stable positional relationship determined by the reoriented magnetic domain.

3. In a method as recited in claim 2 and including the step of maintaining said other body stationary while said one body moves with respect thereto to said second positional relationship.

4. In a method as recited in claim 2 and including the steps of again changing said one magnetic domain orientation and releasing said one body to assume due to natural magnetic interaction with said other body a position providing said first positional relationship for again achieving said first effect, and cyclically repeating said steps for sequentially producing said first and second effects one after the other.

5. In a method as recited in claim 4 and wherein said cyclically repeated steps are identical while said first and second effects produced alternate.

6. In a method as recited in claim 4 and including the step of operating a mechanical motion-transmitting mechanism with said one body for achieving said effects.

7. In a method as recited in claim 2 and including the step of supporting said one body for turning or axial movement with respect to said other body respectively to a pair of different positions with respect to said other body where said first and second positional relationships are provided.

8. In a method as recited in claim 7 and wherein said positions are in angular relationship to each other.

9. In a method as recited in claim 7 and including the step of connecting to said body a control which is operated by said one body to provide for said control first and second positions respectively corresponding to said positional relationships and said effects.

10. In a method as recited in claim 2 and wherein said bodies form part of a vas valve and achieving from said first positional relationship of said bodies a first effect according to which the sperm are prevented from flowing through the vas valve in numbers sufficient for conception, while achieving from the second positional relationship of said bodies a second effect according to which sperm are permitted to flow freely through the vas valve.

11. In a method as recited in claim 2 and wherein said bodies are respectively a solid body which is impermeable to fluid flow and a filter body at least in part which is permeable to fluid flow, both of said bodies being respectively formed with passages extending therethrough, said passages communicating with each other in one of said positional relationships for providing unfiltered flow of fluid through said bodies along said passages thereof as one of said effects, and said passages being out of communication with each other in the other of said positional relationships of said bodies for providing a filtered flow of fluid through said bodies as the other of said effects.

12. In a method as recited in claim 2 and wherein both of said bodies are impermeable to fluid flow while said other body is formed with a fluid-flow passage extending therethrough and said one body is formed with two fluid-flow passages extending therethrough, one of the latter two passages being unobstructed while the other carries a filter for filtering fluid flowing therethrough, said unobstructed passage of said one body communicating with said passage of said other body in one of said positional relationships of said bodies for providing unfiltered fluid flow past both of said bodies as one of said effects, and the other of said passages of said one body communicating with said passage of said other body in the other of said positional relationships for providing filtered fluid flow of a fluid as the other of said effects.

13. In a method as recited in claim 2 and including the step of acting with a detent on at least said one body for precisely determining the position of said one body with respect to the other said body in at least one of said positional relationships.

14. In a method as recited in claim 1 wherein said relationships are force relationships and including the step of directing temporarily through at least one of said bodies a polarizing magnetic field strong enough to change at least one magnetic domain orientation thereby eliminating the first stable force relationship and terminating said magnetic field while maintaining said bodies stationary to produce forces between said bodies to provide a second force relationship.

15. In a method as recited in claim 1 wherein said relationships are positional relationships and wherein said bodies are of a cylindrical configuration and are located coaxially next to each other with said one body being supported for rotation about the common axis of said bodies with respect to the other of said bodies to assume with respect thereto difference angular positions respectively providing said positional relationships, and directing a polarizing magnetic field through at least one of said bodies in a direction normal to the common axis thereof for changing at least said one magnetic domain orientation, and terminating said polarizing magnetic field to provide for said one body a turning movement with respect to the other body to achieve said second positional inter-relationship.

16. In a method as recited in claim 1 and wherein said given magnetic domain orientations provide between said bodies an attraction which places them in engagement with each other for achieving said first effect, and said changed magnetic domain orientation providing a repulsion between said bodies for forcing them apart from each other to achieve said second effect.

17. In an operational control system assembly, at least two magnetically retentive bodies each of which has a given magnetic domain orientation and which remain unaffected under the influence of random disturbances, support means supporting said bodies close enough to each other to permit magnetic interaction, and said support means supporting at least one of said bodies for free movement at least in one direction with respect to the other of said bodies in response to magnetic interaction therebetween for providing a first positional relationship between said bodies, and polarizing magnetic field creating means adapted to be positioned with respect to said bodies for temporarily directing a polarizing magnetic field of a sufficient force which is greater than that of random disturbances along a path which will change at least one of said magnetic domain orientations thereby eliminating said positional relationship so that after said one magnetic domain orientation is changed at least said one body can move with respect to said other body to assume with respect thereto a position providing a second positional relationship between said bodies after said polarizing magnetic field is removed whereby said control system is capable of achieving a different effect.

18. The combination of claim 17 and wherein said support means maintains said other body stationary with respect to said support means, while said support means supports said one body for angular movement with respect to said other body to angular different positions with respect thereto respectively providing said positional relationship, the movement of said one body to each of said angular positions caused by the changed magnetic domain orientation after the polarizing magnetic field is removed.

19. The combination of claim 17 and wherein said polarizing magnetic field creating means when temporarily creating said polarizing magnetic field at successive intervals successively changing said one magnetic domain orientation from said given magnetic domain orientation to said changed magnetic domain orientation, so that said one body can sequentially move to said positions with respect to said other body after successive changes of said one magnetic domain orientation.

20. The combination of claim 17 and wherein a valve means is operatively connected with said one body to be operated thereby for opening and closing a path of fluid flow as said one body now turns to said positions with respect to said other body.

21. The combination of claim 17 and wherein a mechanical transmission means is operatively connected with said one body to be operated thereby for mechanically moving a given component between two different positions when said one body moves to said different positions with respect to said other body.

22. The combination of claim 17 and wherein said given magnetic orientation of said bodies provides an attraction therebetween, while said support means supports at least said one body for movement toward and away from the other body with said one body engaging said other body as a result of the attraction therebetween when said bodies respectively have said given magnetic domain orientations, said polarizing magnetic field creating means changing said one magnetic orientation to provide repulsion between said bodies, so that after said one magnetic domain orientation is changed said one body can move away from said other body.

23. The combination of claim 17 and wherein said bodies are respectively a filter body at least in part for filtering fluid flowing therethrough and a body which is impermeable to fluid flow, both of said bodies respectively being formed with passages extending therethrough, and said support means supporting said one body to assume with respect to said other body a position where said passages are not in communication with each other when said bodies have one of said positional relationships, so that under the latter conditions filtered fluid flow is provided through said bodies, and said support means supporting said one body to assume with respect to said other body in the other of said positional relationships a position where said passages are in communication with each other to change from a filtered fluid flow to an unfiltered fluid flow.

24. The combination of claim 23 and wherein said bodies form part of a vas valve with said filter body having a porosity small enough to preclude flow of sperm therethrough in numbers sufficient to achieve conception.

25. The combination of claim 17 and wherein both of said bodies are impermeable to fluid flow while said other body is formed with a passage extending therethrough and said one body is formed with a pair of passages extending therethrough with one of the latter pair of passages carrying a filter means for filtering fluid flowing through said one of said pair of passages of said one body, and said pair of passages of said one body respectively communicating with said passage of said other body in the two positional relationships between said bodies, so that in the different positions of said one body with respect to said other body there will be provided filtered and unfiltered fluid flow, respectively.

26. The combination of claim 25 and wherein said bodies form part of a vas valve and said filter means is capable of preventing sperm from flowing therethrough in numbers sufficient for conception.

27. The combination of claim 17 and wherein a detent means cooperates with said one body for more precisely aligning the position thereof with respect to said other body.

28. The combination of claim 17 and wherein a detent means cooperates with said one body for identifying said first and second positional relationships.

29. The combination of claim 28 wherein said first and said second positional relationships are detectable from each other by remote excitation of said bodies.

30. The combination of claim 17 and wherein at least one of the said bodies is isotropic.

31. The combination of claim 17 and wherein one of the said bodies is isotropic and the other of said bodies is anisotropic.

32. The combination of claim 17 and wherein said bodies are respectively formed with passages extending therethrough and said support means supporting said one body to assume with respect to said other body a position where said passages are not in communication with each other when said bodies have one of said positional relationships so that under the latter conditions fluid flow is not provided through said bodies and said support means supporting said one body to assume with respect to said other body in the other of said positional relationships a position where said passages are in communication with each other thereby permitting fluid flow.

* * * * *